United States Patent
Hössel et al.

(10) Patent No.: US 6,509,012 B1
(45) Date of Patent: Jan. 21, 2003

(54) AQUEOUS CATIONIC TENSIDE PREPARATIONS, METHOD FOR THE PRODUCTION AND USE THEREOF

(75) Inventors: Peter Hössel, Schifferstadt (DE); Michael Zirnstein, Schriesheim (DE); Walter Schunter, Freinsheim (DE); Friedrich Wirsing, Speyer (DE); Wolfgang Kasel, Nussloch (DE); Knut Oppenländer, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/403,638

(22) PCT Filed: Apr. 16, 1998

(86) PCT No.: PCT/EP98/02241

§ 371 (c)(1), (2), (4) Date: Oct. 25, 1999

(87) PCT Pub. No.: WO98/48778

PCT Pub. Date: Nov. 5, 1998

(30) Foreign Application Priority Data

Apr. 28, 1997 (DE) .......................... 197 17 925

(51) Int. Cl.$^7$ ................................ A61K 7/08
(52) U.S. Cl. .............. 424/70.27; 424/70.1; 424/70.28; 424/401
(58) Field of Search ............ 424/70.1, 70.27, 424/70.28, 401

(56) References Cited

U.S. PATENT DOCUMENTS

| | | | |
|---|---|---|---|
| 4,160,823 A | 7/1979 | Watanabe et al. ............ 424/70 |
| 4,237,064 A | * 12/1980 | Reck | |
| 4,492,802 A | 1/1985 | Rutzen et al. ............ 564/292 |
| 4,976,956 A | 12/1990 | Noe ............. 424/70 |
| 5,501,806 A | * 3/1996 | Farooq et al. | |

FOREIGN PATENT DOCUMENTS

| | | |
|---|---|---|
| AU | 4039495 | 6/1996 |
| DE | 3417646 | 11/1985 |
| EP | 098802 | 1/1984 |
| GB | 2196980 | 5/1988 |

OTHER PUBLICATIONS

Bates, *Handbook of Biochem.*, 1968, pp. J190–J199.
Remington's Pharmaceutical Sciences (18th Ed. Mack Printing Co. PA 1990) p. 351.*

* cited by examiner

*Primary Examiner*—Thurman K. Page
*Assistant Examiner*—Lakshmi Channavajjala
(74) *Attorney, Agent, or Firm*—Keil & Weinkauf

(57) ABSTRACT

The disclosure sets forth aqueous cationic surfactant formulations and a process for their preparation. The formulations contains in solution a) from 10 to 50% by weight of a quaternary ammonium compound of the formula I:

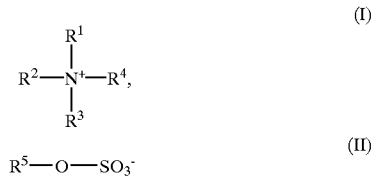

where: the substituents have the meanings set forth in the description, and b) from 0.01 to 15% by weight of an amine of the formula III:

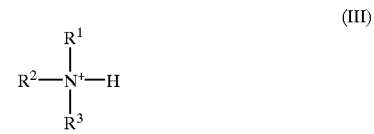

and c) from 0.1 to 5.0% by weight of a buffer which maintains a pH in a range from 4 to 9. The surfactant formulation is prepared by reacting an amine of the formula III

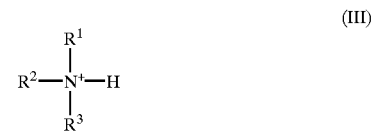

in aqueous solution with a dialkyl sulfate of the formula IV

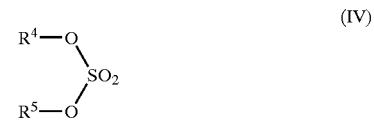

where $R^1$ to $R^5$ are in a molar ratio range from 85 to 99.99 mol %, based on the amine and at from 20 to 100 degrees C. and then adding to the reaction solution from 0.1 to 5.0% by weight of a buffer which maintains a pH in a range from 4 to 9.

8 Claims, No Drawings

AQUEOUS CATIONIC TENSIDE PREPARATIONS, METHOD FOR THE PRODUCTION AND USE THEREOF

The present invention relates to aqueous cationic surfactant formulations, to a process for their preparation and to their use.

Cationic surfactants are sought-after compounds which are used for numerous applications and are described in a large number of publications and patents. For example, DE-A 34 17 646 and DE-A 27 10 468 describe quaternary ammonium compounds as the most important representatives of the cationic surfactants, such as cetyltrimethylammonium chloride or stearyltrimethylammonium chloride, for use in hair after treatment compositions. A disadvantage when using these cationic surfactants is that they have a strong corrosive effect.

EP-B-0 098 802 describes the preparation of quaternary ammonium compounds, for example cetyldimethyl-2-hydroxyethylammonium dihydrogen phosphate with ethylene oxide in the presence of acids, preferably phosphoric acid, and the use of these cationic surfactants in hair cosmetics. Like the abovementioned compounds, these surfactants are easily frozen out of the solutions. Consequently, they have to be dissolved and homogenized before use. Alternatively, they have to be stored in special storage tanks such that they are unable to freeze out. Both measures entail additional costs.

DE-A 31 16 087 describes a process for preparing quaternary ammonium compounds from a tertiary amine and epoxides in the presence of quaternary ammonium compounds as catalyst. This method can be used to prepare cationic surfactants such as 2-hydroxyhexadecyl-2-hydroxyethyldimethylammonium chloride. These compounds too are easily frozen out and have a corrosive effect.

Cationic surfactants are required to have a range of advantageous properties. Examples of important requirements made of such surfactants are 1. good solubilization,
2. good compatibility with anionic surfactants,
3. good foam stabilization,
4. little or no corrosive effect,
5. good biocidal action,
6. good stability on storage,
7. no freezing out from the surfactant solution,
8. absence of halogen,
9. good conditioning effect,
10. good wetting, emulsifying and dispersing capacity, and
11. ease of preparation.

It is an object of the present invention to develop a cationic surfactant which provides as many as possible of these advantageous properties without having the disadvantages of the cationic surfactants known to date. We have found that this object is achieved by the aqueous cationic surfactant formulations of the invention, comprising in solution a) from 10 to 50% by weight of a quaternary ammonium compound of the formula I:

(I)

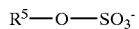

(II)

where:
$R^1$, $R^2$, $R^3$ and $R^4$ independently are substituted or unsubstituted, branched or unbranched $C_1$–$C_4$- or substituted or unsubstituted, branched or unbranched, saturated or unsaturated $C_8$–$C_{16}$-alkyl, at least one and not more than two of $R^1$, $R^2$, $R^3$ and $R^4$ being substituted or unsubstituted, branched or unbranched, saturated or unsaturated $C_8$–$C_{16}$-alkyl, and a water-soluble anion of the Formula (II) is $R^5$—O—$SO_3$—, where $R^5$ is $C_1$–$C_4$-alkyl, b) from 0.01 to 15% by weight of an amine of the Formula III:

(III)

where $R^1$, $R^2$ and $R^3$ are as defined above and not more than two of $R^1$, $R^2$ and $R^3$ are substituted or unsubstituted, branched or unbranched, saturated or unsaturated $C_8$–$C_{16}$-alkyl, and c) from 0.1 to 5.0% by weight of a buffer which maintains a pH in a range from 4 to 9.

In the formulae I and III $R^1$, $R^2$, $R^3$ and $R^4$ independently are substituted or unsubstituted, branched or unbranched $C_1$–$C_4$-alkyl or substituted or unsubstituted, branched or unbranched, saturated or unsaturated $C_8$–$C_{16}$-alkyl, it being possible for at least one and not more than two, of $R^1$, $R^2$, $R^3$ and $R^4$ to be substituted or unsubstituted, branched or unbranched, saturated or unsaturated $C_8$–$C_{16}$-alkyl and advantageous definitions being as follows:

$C_1$–$C_4$-alkyl branched or unbranched $C_1$–$C_4$-alkyl chains such as methyl, ethyl, n-propyl, 1-methylethyl, n-butyl, 1-methylpropyl, 2-methylpropyl or 1,1-dimethylethyl, preferably methyl or ethyl;

$C_8$–$C_{16}$-alkyl: branched or unbranched, saturated $C_8$–$C_{16}$-alkyl chains such as n-octyl, 2-methylheptyl, 3-methylheptyl, 4-methylheptyl, 2,2-dimethylhexyl, 2,3-dimethylhexyl, 2,4-dimethylhexyl, 2,5-dimethylhexyl, 3,3-dimethylhexyl, 2,2,3-trimethylpentyl, 2,2,4-trimethylpentyl, 3,3,2-trimethylpentyl, 3,3,4-trimethylpentyl, 4,4,2-trimethylpentyl, 4,4,3-trimethylpentyl, 2,3,4-trimethylpentyl, 2-ethylhexyl, 3-ethylhexyl, n-nonyl, 3-ethyl-2-methylhexyl, 2-methyloctyl, 4-methyloctyl, n-decyl, n-undecyl, n-dodecyl, n-tridecyl, n-tetradecyl, 3-ethyl-5-isopropyl-4-methyloctyl, n-pentadecyl, n-hexadecyl, or branched or unbranched unsaturated $C_8$–$C_{16}$-alkyl chains, for example branched or unbranched $C_8$–$C_{16}$-alkenyl chains such as 1-octenyl, 2-octenyl, 3-octenyl, 4-octenyl, 5-octenyl, 6-octnyl or 7-octenyl, nonenyl, decenyl, undecenyl, dodecenyl, tridecenyl, tetradecenyl, n-pentadecenyl, or n-hexadecenyl; preference is given to saturated and unsaturated alkyls or alkenyls which can be derived from amines of fatty alcohols such as caproyl alcohol, enanthyl alcohol, caprylyl alcohol, pelargonyl alcohol, capryl alcohol, lauryl alcohol, myristyl alcohol, pentadecanol, or cetyl alcohol, or amines of linear Ziegler alcohols (amination of the alcohols to the amine); particular preference is given to saturated $C_{12-16}$-alkyl chains and very particular preference to saturated $C_{12}$–$C_{14}$-alkyl chains which can be prepared on the basis, for example, of coconut oil or palm kernel oil. Advantageous branched alkyls can be prepared, for example, on the basis of alcohols from the Guerbet reaction or the oxo reaction.

Examples of substituents of $R^1$, $R^2$, $R^3$ and $R^4$ are alkyl, hydroxylalkyl or hydroxylalkyl ether radicals.

$R^5$ in the formula II is, advantageously, substituted or unsubstituted, branched or unbranched $C_1$–$C_4$-alkyl such as methyl, ethyl, n-propyl, 1-methylethyl, n-butyl, 1-methylpropyl, 2-methylpropyl, or 1,1-dimethylethyl, preferably methyl or ethyl. Suitable substituents of $R^5$ are alkyl, hydroxyalkyl or hydroxyalkyl ether radicals.

The content of quaternary ammonium compounds (a) of the formula I is in a range from 10 to 50% by weight, preferably from 15 to 40% by weight and, with particular preference, from 20 to 35% by weight, based on the overall weight of the surfactant formulation. Particularly preferred cationic surfactants in the surfactant formulation of the invention are surfactants having only one $C_8$–$C_{16}$-alkyl chain, preferably a $C_{12}$–$C_{16}$-alkyl chain and, with particular preference, with a $C_{12}$–$C_{14}$-alkyl chain, as in N,N,N-trimethyl-$C_{12}/C_{14}$-ammonium methyl sulfate.

The content of amines (b) of the Formula II is in a range from 0,01 to 15 % by weight, preferably from 0,1 to 10 % by weight and, with particular preference, from 0.5 to 5 % by weight, based on the overall weight of the surfactant formulation. Particularly preferred amines in the surfactant formulation of the invention are those having a long $C_8$–$C_{16}$-alkyl chain, preferably with a $C_{12}$–$C_{16}$-alkyl chain and, with particular preference, with a $C_{12}$–$C_{14}$-alkyl chain and two short $C_1$–$C_4$-alkyl chains, such as N,N-dimethyl-$C_{12}/C_{14}$-amine.

It has been found that by adding the buffer to the surfactant solution it is possible to bring about a marked improvement in the stability of the surfactant solution on storage without affecting the surfactant activity. Furthermore, it has likewise been possible to bring about a marked improvement in the solubilizer effect of the surfactant solution by adding the buffer.

The surfactant formulations of the invention comprise advantageously from 0.1 to 5.0% by weight, preferably from 0.5 to 4% by weight, and, with particular preference, from 1.0 to 3.5% by weight of buffer (c) based on the overall weight of the surfactant formulation.

Suitable buffers for the aqueous cationic surfactant formulations of the invention are in principle all those known buffers which maintain a pH in a range from 4 to 9, preferably from 5 to 8 and, with particular preference, from 6 to 8, as described, for example, in Handbook of Biochemistry (Eds. Sober, H. A., Horte R. A., The Chemical Rubber Co., 1968: J-195–J-199).

Examples of suitable buffers are all salts of weak acids and strong bases or of strong acids and weak bases, which can be salts of the same acids and bases or mixtures of different acids or bases.

Suitable examples of buffers are those such as Walpole buffer (acetic acid/Na acetate), Gomori aconitate buffer (aconitic acid/NaOH), Kolthoff buffer (borax/succinate), Sörensen's citrate II buffer (disodium citrate/NaOH), McIlvaine's Citric acid/phosphate buffer (citric acid/disodium phosphate), Stafford, Watson and Rand's dimethylglutaric acid buffer (dimethylglutaric acid/NaOH), Sörensen's phosphate buffer (potassium/dihydrogen phosphate/disodium hydrogen phosphate), Gomori trismaleate buffer (trismaleate/NaOH) or Gomori succinate buffer (succinate/NaOH). Other suitable buffers include MES, ADA, PIPES, BIS-TRIS, MOPSO, BIS-TRIS PROPANE, MOPS, DIPSO, TAPSO, HEPPSO, POPSO, EPPS, TEA, TAPS or ACES, which are customary buffers in biochemistry, or amino acid buffers. Preference is given to buffers which can be prepared advantageously from weak acids and their salts, examples being sodium acetate/acetic acid, sodium citrate/citric acid, sodium borate/boric acid, sodium phosphate/phosphoric acid, potassium phosphate/phosphoric acid, hydrogen carbonate/soda, sodium hydroxide/citric acid, sodium hydroxide/tartaric acid or mixtures thereof. Further suitable buffers include cholamine chloride, BES, TES, HEPES, acetamidoglycine, glycinamide, tris, bicine, tricine, glycylglycine or buffers based on ethanolamine or diethanolamine.

Individual buffers or mixtures can be used in the surfactant formulation of the invention.

Particular preference is given to the use of buffers or buffer mixtures based on hydrogen phosphate/dihydrogen phosphate, such as sodium phosphate/phosphoric acid, potassium phosphate/phosphoric acid, disodium hydrogen phosphate/sodium dihydrogen phosphate, dipotassium hydrogen phosphate/potassium dihydrogen phosphate or KOH/$H_3PO_4$ or NaOH/$H_3PO_4$, since in addition to the advantageous effects mentioned above these are known to have a corrosion protection effect.

Another advantageous property of the surfactant formulations of the invention is excellent stability on cold storage; in other words, the formulations do not freeze out below 20° C. Unlike the commercial products they show no precipitation or inhomogeneity below this temperature. This is due firstly to the preferred length of the longer alkyl chains of $C_8$–$C_{16}$, where the proportion of the $C_{16}$-alkyl chain within the alkyl chain distribution should be as low as possible, and secondly to the buffer. With high proportions of $C_{16}$-alkyl chains, the cold stability of the surfactant formulations of the invention may decrease.

The surfactant formulations of the invention may if desired comprise further additives or auxiliaries known to the skilled worker, such as electrolytes for increasing the viscosity, sodium chloride or other customary salts, hydroxyalkylcellulose, cationic celluloses, cationic synthetic polymers, other cationic surfactants, such as Dehyquart® grades or Luviquat® grades, alkyl ether sulfates or alkyl polyglycosides, or may if desired be combined with further surfactants, for example with cationic or anionic surfactants.

The surfactant formulations of the invention can be synthesized by a range of methods known to the skilled worker, for example using alkylating agents such as alkyl sulfates, alkylsulfonates, alkyl halides or other active esters based on various amines as starting substances; advantageously, the process of the invention is used for the synthesis.

The process of the invention which has been found for preparing compounds of the formula I comprises reacting amines of the formula III

(III)

in aqueous solution with a dialkyl sulfate of the formula IV

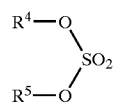

(IV)

where $R^1$ to $R^5$ are as defined above in a molar ratio range from 85 to 99.99 mol % based on the amine and at from 20 to 100° C. and then adding to the reaction solution from 0.1 to 5.0% by weight of a buffer which maintains a pH in a range from 4 to 9.

In the process of the invention the dialkyl sulfate is advantageously used in a molar ratio of from 85 to 99.9 mol %, preferably from 95 to 99.5 mol %, and with particular preference, from 97.0 to 99.0 mol % based on the amine (=100 mol %), so that there is always an excess of amine and so that the monoalkyl sulfate formed in the reaction is present in the surfactant formulation in no more than equimolar amounts with respect to the quaternary ammonium compound that is formed.

The reaction is advantageously carried out at from 20 to 100° C., preferably from 40 to 90° C. and, with particular preference from 50 to 80° C.

The alkylation can be conducted with or without pH control; in the former case, by adding sodium or potassium hydroxide solution, for instance. It is preferred not to control the pH. The sodium or potassium hydroxide solution added if pH control is carried out can advantageously later become a constituent of the buffer.

In the process of the invention it is advantageous to react an initial charge of aqueous alkylamine solution, emulsion or suspension with the dialkyl sulfate which is metered in. The metered addition of the dialkyl sulfate is in this case advantageously controlled such that the abovementioned temperature ranges are not exceeded. In principle, it is also possible to have the dialkyl sulfate as the initial charge and to meter in the alkyl amine, or to conduct the reaction in the mixing chamber with simultaneous addition of the reactants. In order to facilitate rapid addition of the dialkyl sulfate the reaction is advantageously conducted with cooling and under inert conditions, although cooling is generally not necessary.

In a preferred embodiment, the buffer can be added after alkylation to the reaction solution, it being possible for the buffer to be produced in the solution—which is preferred— or else to be added as a ready-made buffer to the reaction solution. The buffers can be used in the form of solutions or as solids. In principle the buffer can be added before, during or after the alkylation reaction, the latter being preferred.

The cationic surfactant formulations of the invention are suitable for a range of applications, preferably for cosmetics, for example in cosmetic formulations having care and/or conditioning properties, examples being styling products such as hair mousses, hair gels or hairsprays or after treatment compositions such as hair lotions, treatment rinses, treatment packs, treatment fluids for damaged ends, hair repair compositions, hot oil treatments, shampoos, liquid soaps or beauty creams.

The surfactant formulations are suitable as hydrophobicizers, as antistats, for coating textiles or leather, as electroplating auxiliaries, as metal cleaning assistants, as corrosion inhibitors, as flocculants or coagulants, as textile printing auxiliaries, for printing inks and printing plates, as dispersants for paints and coatings, as auxiliaries for the electrical and electronics industry, as biocides and as constituents of disinfectants, as pharmaceutical auxiliaries or for animal cosmetics. The surfactant formulations of the invention are also suitable as initiators for cationic polymerization, as polymerization media or as binders for bitumen.

EXAMPLES

Example 1

Preparing the Cationic Surfactant Formulation 72.0 kg of deionized water and 25.0 kg of N,N-dimethylcocoamine (70–75% dodecyl, 23–28% tetradecyl, 0–2% decyl, 0–2 % hexadecyl; amine number 4.22–4.55 mmol of basic N/g) were charged to a stirred reactor for preparing N,N,N-trimethylcocoalkylammonium methosulfate (INSI name: cocotrimonium methosulfate). 13.9 kg of dimethyl sulfate were added under inert gas and with stirring at 65–70° C. at a rate such that the temperature could be maintained. After cooling to 50° C., 1.40 kg of 85% strength phosphoric acid, 1.70 kg of 50% strength potassium hydroxide solution and 14.3 kg of deionized water were added.

Product: 126 kg of aqueous product solution having a Gardner color number of <1, Dimethyl sulfate below the detection limit;

Nonvolatiles content: 31%

Basic nitrogen: 0.07%

Example 2

Comparative Performance Testing of Various Products Comprising Cationic Surfactants The surfactant formulations preparable with ease as described in Example 1 exhibited a range of performance advantages such as good stability on cold storage; in other words, 25 to 30 % strength surfactant solutions showed no precipitation or inhomogeneity below 20° C. Heating the surfactant solution before use and/or mechanically stirring it to maintain a clear solution are unnecessary. Moreover, the solutions prepared in Example 1 are noncorrosive, have a good solubilizer effect and overall are stable on storage. There is no change in the surfactant solutions even over a prolonged storage period (several weeks). These advantageous properties can be attributed to the combination of the specific quaternary ammonium compounds, the amine and the buffer.

Table 1 compares the surfactant formulations of the invention with various market products, and in so doing makes these advantageous properties very evident. All of the comparison products, Luviquat® Mono CP (cetylhydroxyethyldimethylammonium dihydrogen phosphate), Dehyquart® A (cetyltrimethylammonium chloride), Dehyquart® E [N-(2-Hydroxyhexadec-1-yl)-N,N-dimethyl-N-2-hydroxyethylammonium chloride], Dehyquart® SP (trisoligooxyethylalkylammonium phosphate), have disadvantages in terms of stability on cold storage relative to the surfactant formulations of the invention as prepared in Example 1 (Luviquat® Mono LS=N,N,N-trimethyl-$C_{12}/C_{14}$-ammonium methyl sulfate, see Table 1).

TABLE 1

Results of the performance tests

| Surfactants | Stability on cold storage | Conditioning effect | Foam stabilizing effect | Compatability with anionic surfactants | Solubilizer effect | Halogen-free |
|---|---|---|---|---|---|---|
| Luviquat ® Mono LS | yes | very good | very good | very good | good | yes |
| Luviquat ® Mono CP | no | very good | very good | very good | poor | yes |
| Dehyquart ® A | no | very good | very good | poor | good | no |
| Dehyquart ® E | no | very good | very good | good | good | no |
| Dehyquart ® SP | no | very good | very good | good | poor | yes |

The properties indicated in Table 1 were assessed by the following methods.

Stability on Cold Storage

To determine the stability on cold storage the various surfactant solutions were stored in a long-term test at 6° C. for one year and then examined for any instances of clouding or precipitation. In a rapid test, the samples were cooled from 20° C. to −18° C. and then thawed again, and then again examined for any instances of clouding or precipitation.

Conditioner Effect

The conditioner effect was determined in a subjective test of the wet-combability of locks of test hair. For this purpose the locks of hair were treated with the cationic surfactant solutions or formulations and then the combability was assessed by three independent individuals as very good, good or poor.

Foam Stabilizer Effect

To determine the foam stabilizer effect the surfactants were used to produce foams, the foam quality was assessed, and the stability of the foams over time was measured.

Compatibility with Anionic Surfactants

The compatibility with anionic surfactants was tested in a 4 % mixture of the surfactants (content of active substance) with 50 % Texapon NS0 (=28% of sodium lauryl ether sulfate in water). A clear solution of the mixture was assessed as very good, slight clouding as good, and precipitation in the mixture earned a rating of poor.

Solubilizer Effect

The solubilizer effect was tested with nine different customary cosmetic oils (see Table 2). The effect of the surfactants was assessed after 24 hours. The assessment was good if six or more of the oils were solubilized.

TABLE 2

Solubilizer effect of various surfactants

| Oil | Luviquat ® Mono LS | Luviquat ® Mono CP | Dehyquart ® A | Dehyquart ® E | Dehyquart ® SP |
|---|---|---|---|---|---|
| 1.0% Dwarf pine[a] | separated | separated | cloudy | cloudy | separated |
| 1.0% Spruce needle[a] | separated | separated | separated | separated | separated |
| 1.0% Rosemary[a] | separated | separated | separated | separated | separated |
| 1.0% Lavender[a] | clear | separated | clear | clear | clear |
| 1.0% Oral care aroma oil[a] | clear | almost clear | clear | clear | clear |
| 1.0% Blue Water[a] | clear | cloudy | clear | clear | clear |
| 0.2% Perfume oil "Cinderella"[b] | clear | cloudy | clear | clear | separated |
| 0.1% Perfume oil "Louissa"[b] | clear | clear | clear | separated | clear |
| 0.1% Perfume oil "Sport"[b] | clear | almost clear | clear | clear | clear |

[a] solubilized with 3% of the active surfactant component
[b] solubilized with 0.6% of the active surfactant component

What is claimed is:

1. An aqueous cationic surfactant formulation comprising
   a) from 10 to 50% by weight of a quaternary ammonium compound of the formula I:

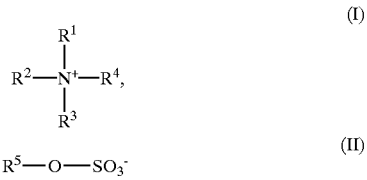

where $R^1$, $R^2$, $R^3$, $R^4$, $R^5$ are:
$R^1$, $R^2$, $R^3$ and $R^4$ independently are hydroxyalkyl- or hydroxyalkyl ether-substituted or unsubstituted, branched or unbranched $C_1$–$C_4$- or hydroxyalkyl- or hydroxyalkyl ether-substituted or unsubstituted, branched or unbranched, saturated or unsaturated $C_8$–$C_{16}$-alkyl, at least one and not more than two of $R^1$, $R^2$, $R^3$ and $R^4$ being hydroxyalkyl- or hydroxyalkyl ether-substituted or unsubstituted, branched or unbranched, saturated or unsaturated $C_8$–$C_{16}$-alkyl, and a water-soluble anion of the formula (II) is $R^5$—O—$SO_3^-$, where $R^5$ is $C_1$–$C_4$-alkyl, b) from 0.01 to 15% by weight of an amine of the formula III:

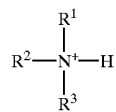
(III)

where $R^1$, $R^2$ and $R^3$ are as defined above and not more than two of $R^1$, $R^2$ and $R^3$ are hydroxyalkyl- or hydroxyalkyl ether substituted or unsubstituted, branched or unbranched, saturated or unsaturated $C_8$–$C_{16}$-alkyl, and c) from 0.1 to 5.0% by weight of a buffer which maintains a pH in a range from 4 to 9.

2. A surfactant formulation as claimed in claim 1 comprising as quaternary ammonium compound N,N,N-trimethyl-$C_{12}$–$C_{14}$- alkylammonium methosulfate.

3. A surfactant formulation as claimed in claim 1 comprising as amine N,N-dimethyl-$C_{12}$–$C_{14}$-alkylamine.

4. A surfactant formulation as claimed in claim 1 comprising as buffer a hydrogen/dihydrogen phosphate buffer.

5. A process for preparing a surfactant formulation as claimed in claim 1, which comprises reacting an amine of the formula III

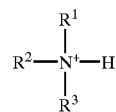
(III)

in aqueous solution with a dialkyl sulfate of the formula IV

(IV)

where $R^1$ to $R^5$ are as defined in claim 1 in a molar ratio range from 85 to 99.99 mol %, based on the amine and at from 20 to 100° C. and then adding to the reaction solution from 0.1 to 5.0% by weight of a buffer which maintains a pH in a range from 4 to 9.

6. A method of treating hair comprising the step of applying to the hair an effective amount of the surfactant composition as defined in claim 1.

7. A cosmetic composition containing a surfactant composition as claimed in claim 1.

8. A hairsetting agent, hair rinse, hair spray, permanent waving composition or hair coloring composition containing an effective amount of a surfactant composition as claimed in claim 1.

* * * * *